(12) United States Patent
Bloom

(10) Patent No.: US 7,928,148 B2
(45) Date of Patent: Apr. 19, 2011

(54) HYDROGENOLYSIS OF GLYCEROL AND PRODUCTS PRODUCED THEREFROM

(75) Inventor: Paul Bloom, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 28 days.

(21) Appl. No.: 11/876,912

(22) Filed: Oct. 23, 2007

(65) Prior Publication Data

US 2008/0103339 A1     May 1, 2008

Related U.S. Application Data

(60) Provisional application No. 60/853,574, filed on Oct. 23, 2006.

(51) Int. Cl.
*A01N 31/00*     (2006.01)
(52) U.S. Cl. ..................................................... 514/738
(58) Field of Classification Search .................. 514/738
See application file for complete search history.

(56) References Cited

U.S. PATENT DOCUMENTS

| | | |
|---|---|---|
| 4,401,823 A | 8/1983 | Arena |
| 5,354,914 A | 10/1994 | Gubitosa et al. |
| 6,291,725 B1 | 9/2001 | Chopade et al. |
| 6,479,713 B1 | 11/2002 | Werpy et al. |
| 6,570,043 B2 | 5/2003 | Elliot et al. |
| 6,670,300 B2 | 12/2003 | Werpy et al. |
| 6,841,085 B2 | 1/2005 | Werpy et al. |
| 2005/0244312 A1 | 11/2005 | Suppes et al. |
| 2007/0131579 A1 | 6/2007 | Koivusalmi et al. |
| 2007/0200087 A1 | 8/2007 | Wehner et al. |

FOREIGN PATENT DOCUMENTS

| | | |
|---|---|---|
| EP | 0523014 A2 | 1/1993 |
| EP | 0523015 A2 | 1/1993 |
| WO | 2005051874 A1 | 6/2005 |
| WO | 2007095255 A2 | 8/2007 |

OTHER PUBLICATIONS

CAS registry names for 1,2- and 1,3-propanediol.*
Standard Test Methods for Determining the Biobased Content of Natural Range Materials Using Radiocarbon and Isotope Ratio Mass Spectrometry Analysis, ASTM International, Designation: D 6866-05, 14pgs., USA, 1986.
Y Kusunoki et al., Highly active metal-acid bifunctional catalyst system for hydrogenolysis of glycerol under mild reaction conditions, Catalysis Communications, 2005,pp. 645-648, USA.
S.P.Crabtree et al., Optimize Glycol Production from Biomass, Davy Process Technology, Clean Fuels Special Report, London UK, Feb. 2006, pp. 87-92, USA.
Ira T. Clark, Hydrogenolysis of Sorbitol, Industrial and Engineering Chemistry, Madison Wisconsin, Aug. 1958, pp. 1125-1126, vol. 50, No. 8, USA.
T. Miyazawa et al., Glycerol conversion in the aqueous solution under hydrogen over Ru/C + an ion-exchange resin and its reaction mechanism, Institute of Materials Science, Journal of Catalysis, Japan, 2006, pp. 213-221, USA.
Walter Zartman et al., Hydrogenolysis of Sugars, Communication from the laboratory of Organic Chemistry, Wisconsin, Nov. 1933,pp. 4559-4563, vol. 55, USA.

* cited by examiner

*Primary Examiner* — Elvis O Price
(74) *Attorney, Agent, or Firm* — William B. Miller

(57) ABSTRACT

Processes for the hydrogenolysis of glycerol, as well as products produced therefrom are disclosed.

11 Claims, 11 Drawing Sheets

Table 5A: Hydrogenolysis of 40% USP Glycerol Feed using a solid phase catalyst

| Test No. | Temperature | | | H2 Press. (psi) | NaOH (%) w/w | LHSV | Conversion (%) | PG Selectivity (%) | EG Yield (%) | Lactic Yield (%) | EtOH Yield (%) | MeOH Yield (%) |
|---|---|---|---|---|---|---|---|---|---|---|---|---|
| | Top | Mid | Bottom | | | | | | | | | |
| 248 | 183 | 191 | 199 | 1600 | 1 | 2.3 | 47.7 | 92.1 | 1.4 | 0.5 | 0 | 0.7 |
| 249 | 184 | 191 | 199 | 1600 | 1 | 1.8 | 56.7 | 90.8 | 1.8 | 0.6 | 0 | 0.9 |
| 250 | 185 | 193 | 199 | 1600 | 1 | 1.5 | 63.3 | 90.7 | 2.1 | 0.7 | 0.1 | 0.9 |
| 205 | 178 | 190 | 198 | 1200 | 1.2 | 1.8 | 50 | 94 | 1.6 | 1 | 0.1 | 0 |
| 257 | 184 | 195 | 206 | 1600 | 1 | 1.8 | 59.2 | 92.6 | 2.1 | 0.7 | 0.1 | 1 |
| 264 | 178 | 190 | 196 | 1600 | 1.9 | 1.6 | 59.3 | 90.3 | 1.9 | 0.9 | 0 | 1 |
| 261 | 184 | 194 | 200 | 1600 | 1 | 1.5 | 59.4 | 90.4 | 2 | 0.7 | 0.1 | 1.1 |
| 242 | 185 | 194 | 205 | 1600 | 0.7 | 1.8 | 65.2 | 92.2 | 1.5 | 0.5 | 0 | 0.7 |
| 199 | 154 | 177 | 194 | 1200 | 1.2 | 1.8 | 67 | 86.6 | 2.2 | 1.1 | 0.3 | 1 |
| 262 | 183 | 196 | 202 | 1600 | 1.5 | 1.5 | 67.2 | 89.6 | 2.4 | 0.9 | 0.1 | 1.3 |
| 263 | 181 | 193 | 199 | 1600 | 1.9 | 1.6 | 68.8 | 89.1 | 2.4 | 1.1 | 0.1 | 1.2 |
| 180 | 178 | 191 | 202 | 1200 | 1.1 | 1 | 76.7 | 80.7 | 2.7 | 1.5 | 0.7 | 1.3 |
| 256 | 189 | 206 | 217 | 1600 | 0.8 | 1.8 | 77.1 | 87.6 | 3.1 | 1 | 0.2 | 1.5 |
| 254 | 193 | 211 | 223 | 1600 | 1 | 1.8 | 81.2 | 90.6 | 3.8 | 1.2 | 0.3 | 1.8 |
| 255 | 191 | 209 | 221 | 1600 | 0.8 | 1.8 | 86.2 | 73.6 | 3.2 | 1 | 0.2 | 1.6 |
| 228 | 193 | 228 | 229 | 1600 | 1.4 | 1.8 | 93.1 | 83.2 | 4.3 | 1.9 | 1 | 0.6 |
| 240 | 188 | 212 | 226 | 1600 | 1.3 | 1.8 | 93 | 82.2 | 3.8 | 1.8 | 1 | 1.7 |
| 164 | 183 | 203 | 207 | 1200 | 1.1 | 1 | 94.6 | 87.7 | 3.6 | 1.8 | 0.6 | 1.7 |
| 166 | 188 | 211 | 216 | 1200 | 1.5 | 1 | 95.4 | 60.7 | 2.8 | 1.5 | 0.7 | 2 |
| 191 | 165 | 205 | 227 | 1200 | 1.6 | 1.8 | 96.4 | 69.6 | 3.6 | 2.8 | 2.1 | 1.4 |

FIGURE 2A

Table 5B: Hydrogenolysis of 40% USP Glycerol Feed using a solid phase catalyst

| Test No. | Temperature | | | PG Yield (%) | Butanediol's (g/100g) | | | | | Total BDO (g/100 g) |
|---|---|---|---|---|---|---|---|---|---|---|
| | Top | Mid | Bottom | | 1-2 BDO | 1-3 BDO | 1-4 BDO | 2-3 BDO | 2-4 PeDO | Total BDOs (g/100g) | on PG basis |
| 248 | 183 | 191 | 199 | 36.3 | 0 | 0 | 0 | 0.04 | 0 | 0.04 | 0.11 |
| 249 | 184 | 191 | 199 | 42.4 | 0 | 0 | 0 | 0.05 | 0 | 0.05 | 0.12 |
| 250 | 185 | 193 | 199 | 47.3 | 0.02 | 0 | 0 | 0.09 | 0.01 | 0.12 | 0.25 |
| 205 | 178 | 190 | 198 | 38 | 0.03 | 0 | 0 | 0.16 | 0.03 | 0.22 | 0.58 |
| 257 | 184 | 195 | 206 | 45.3 | 0 | 0.02 | 0 | 0.05 | 0 | 0.07 | 0.15 |
| 264 | 178 | 190 | 196 | 44.3 | 0 | 0.01 | 0 | 0.05 | 0 | 0.06 | 0.13 |
| 261 | 184 | 194 | 200 | 44.4 | 0 | 0 | 0 | 0.05 | 0 | 0.05 | 0.11 |
| 242 | 185 | 194 | 205 | 33.2 | 0.05 | 0 | 0 | 0.26 | 0.04 | 0.35 | 1.05 |
| 199 | 154 | 177 | 194 | 47.9 | 0.07 | 0 | 0 | 0.38 | 0.08 | 0.53 | 1.1 |
| 262 | 183 | 196 | 202 | 49.8 | 0 | 0 | 0 | 0.08 | 0.01 | 0.09 | 0.18 |
| 263 | 181 | 193 | 199 | 50.6 | 0 | 0.01 | 0 | 0.1 | 0.01 | 0.12 | 0.24 |
| 180 | 178 | 191 | 202 | 51 | 0.1 | 0 | 0 | 0.57 | 0.14 | 0.81 | 1.58 |
| 256 | 189 | 206 | 217 | 55.9 | 0 | 0.04 | 0 | 0.17 | 0.02 | 0.23 | 0.41 |
| 254 | 193 | 211 | 223 | 60.8 | 0 | 0.06 | 0 | 0.29 | 0.04 | 0.39 | 0.63 |
| 255 | 191 | 209 | 221 | 52.4 | 0 | 0.06 | 0 | 0.29 | 0.04 | 0.39 | 0.74 |
| 228 | 193 | 228 | 229 | 64 | 0.14 | 0 | 0 | 0.69 | 0.14 | 0.97 | 1.5 |
| 240 | 188 | 212 | 226 | 63.1 | 0.19 | 0 | 0 | 1.05 | 0.23 | 1.47 | 2.3 |
| 164 | 183 | 203 | 207 | 68.6 | 0.12 | 0 | 0 | 0.61 | 0.12 | 0.85 | 1.23 |
| 166 | 188 | 211 | 216 | 47.7 | 0.12 | 0 | 0 | 0.81 | 0.19 | 1.12 | 2.31 |
| 191 | 165 | 205 | 227 | 55.4 | 0.23 | 0 | 0 | 1.65 | 0.43 | 2.31 | 4.05 |

FIGURE 2B

Table 6. Hydrogenolysis of 40% USP Glycerol Feed using a solid phase catalyst.

| Run # | Temperature | | | H₂ Press. (psi) | NaOH (%) w/w | LHSV | Conversion (%) | PG Yield (%) | PG Selectivity (%) | Butanediol's (g/100g) | | | 2,3-BDO (g/100 g) on PG basis | Total BDO (g/100 g) on PG basis |
|---|---|---|---|---|---|---|---|---|---|---|---|---|---|---|
| | Top | Mid | Bottom | | | | | | | 1-2 BDO | 1-3 BDO | 2-3 BDO | | |
| 248 | 183 | 191 | 199 | 1600 | 1 | 2.3 | 47.7 | 36.3 | 92.1 | 0 | 0 | 0.04 | 0.11 | 0.11 |
| 249 | 184 | 191 | 199 | 1600 | 1 | 1.8 | 56.7 | 42.4 | 90.8 | 0 | 0 | 0.05 | 0.12 | 0.12 |
| 250 | 185 | 193 | 199 | 1600 | 1 | 1.5 | 63.3 | 47.3 | 90.7 | 0.02 | 0 | 0.09 | 0.19 | 0.23 |
| 205 | 178 | 190 | 198 | 1200 | 1.2 | 1.8 | 50 | 38 | 94 | 0.03 | 0 | 0.16 | 0.42 | 0.50 |
| 257 | 184 | 195 | 206 | 1600 | 1 | 1.8 | 59.2 | 45.3 | 92.6 | 0 | 0.02 | 0.05 | 0.11 | 0.15 |
| 264 | 178 | 190 | 196 | 1600 | 1.9 | 1.6 | 59.3 | 44.3 | 90.3 | 0 | 0.01 | 0.05 | 0.11 | 0.13 |
| 261 | 184 | 194 | 200 | 1600 | 1 | 1.5 | 59.4 | 44.4 | 90.4 | 0 | 0 | 0.05 | 0.11 | 0.11 |
| 242 | 185 | 194 | 205 | 1600 | 0.7 | 1.8 | 65.2 | 33.2 | 92.2 | 0.05 | 0 | 0.26 | 0.78 | 0.93 |
| 199 | 154 | 177 | 194 | 1200 | 1.2 | 1.8 | 67 | 47.9 | 86.6 | 0.07 | 0 | 0.38 | 0.79 | 0.94 |
| 262 | 183 | 196 | 202 | 1600 | 1.5 | 1.5 | 67.2 | 49.8 | 89.6 | 0 | 0 | 0.08 | 0.16 | 0.16 |
| 263 | 181 | 193 | 199 | 1600 | 1.9 | 1.6 | 68.8 | 50.6 | 89.1 | 0 | 0.01 | 0.1 | 0.2 | 0.22 |
| 180 | 178 | 191 | 202 | 1200 | 1.1 | 1 | 76.7 | 51 | 80.7 | 0.1 | 0 | 0.57 | 1.11 | 1.30 |
| 256 | 189 | 206 | 217 | 1600 | 0.8 | 1.8 | 77.1 | 55.9 | 87.6 | 0 | 0.04 | 0.17 | 0.3 | 0.37 |
| 254 | 193 | 211 | 223 | 1600 | 1 | 1.8 | 81.2 | 60.8 | 90.6 | 0 | 0.06 | 0.29 | 0.47 | 0.57 |
| 255 | 191 | 209 | 221 | 1600 | 0.8 | 1.8 | 86.2 | 52.4 | 73.6 | 0 | 0.06 | 0.29 | 0.55 | 0.66 |
| 228 | 193 | 228 | 229 | 1600 | 1.4 | 1.8 | 93.1 | 64 | 83.2 | 0.14 | 0 | 0.69 | 1.07 | 1.29 |
| 240 | 188 | 212 | 226 | 1600 | 1.3 | 1.8 | 93 | 63.1 | 82.2 | 0.19 | 0 | 1.05 | 1.64 | 1.94 |
| 164 | 183 | 203 | 207 | 1200 | 1.1 | 1 | 94.6 | 68.6 | 87.7 | 0.12 | 0 | 0.61 | 0.88 | 1.05 |
| 166 | 188 | 211 | 216 | 1200 | 1.5 | 1 | 95.4 | 47.7 | 60.7 | 0.12 | 0 | 0.81 | 1.67 | 1.92 |
| 191 | 165 | 205 | 227 | 1200 | 1.6 | 1.8 | 96.4 | 55.4 | 69.6 | 0.23 | 0 | 1.65 | 2.89 | 3.29 |

FIGURE 3

Table 7.

| Exp # | Reactor Temperature | | | H$_2$ Press. (psi) | NaOH (%) w/w | LHSV | Conversion (%) | PG Yield (%) | Butanediols (g/100g) | | 2,3-BDO (g/100 g) on PG basis | Total BDO (g/100 g) on PG basis |
|---|---|---|---|---|---|---|---|---|---|---|---|---|
| | Top | Mid | Bottom | | | | | | 1-2 BDO | 2-3 BDO | | |
| 25 | 167 | 170 | 168 | 1000 | 0.46 | 0.54 | 28 | 21 | 0.0075 | 0.01 | 0.12 | 0.21 |
| 5 | 150 | 166 | 169 | 1000 | 2.4 | 0.6 | 75 | 57 | 0.0075 | 0.04 | 0.18 | 0.21 |
| 6 | 150 | 166 | 169 | 1000 | 0.5 | 2 | 14 | 10 | 0.0075 | 0.0075 | 0.19 | 0.38 |
| 27 | 155 | 170 | 170 | 1000 | 2.46 | 1.8 | 32 | 24 | 0.0075 | 0.04 | 0.42 | 0.50 |
| 16 | 201 | 211 | 207 | 1000 | 0.5 | 0.6 | 84 | 54 | 0.1 | 0.67 | 3.02 | 3.47 |
| 26 | 206 | 209 | 203 | 1000 | 2.44 | 0.57 | 97 | 51 | 0.32 | 1.99 | 8.91 | 10.34 |
| 21 | 180 | 205 | 210 | 1000 | 0.5 | 1.9 | 47 | 33 | 0.05 | 0.36 | 2.68 | 3.05 |
| 9 | 171 | 212 | 208 | 1000 | 2.5 | 1.8 | 97 | 60 | 0.2 | 1.55 | 6.07 | 6.85 |

FIGURE 4

Table 8.

| Exp | Temperature | | | H₂ Press. | NaOH | LHSV | Conversion | PG Yield | Butanediols (g/100g) | | 2,3-BDO (g/100 g) on PG basis | Total BDO (g/100 g) on PG basis |
|---|---|---|---|---|---|---|---|---|---|---|---|---|
| # | Top | Mid | Bottom | (psi) | (%) w/w | | (%) | (%) | 1-2 BDO | 2-3 BDO | | |
| 6 | 150 | 166 | 169 | 1000 | 0.5 | 2 | 14 | 10 | 0.0075 | 0.0075 | 0.19 | 0.38 |
| 21 | 180 | 205 | 210 | 1000 | 0.5 | 1.9 | 47 | 33 | 0.005 | 0.36 | 2.68 | 3.05 |
| 25 | 167 | 170 | 168 | 1000 | 0.46 | 0.54 | 28 | 21 | 0.0075 | 0.01 | 0.12 | 0.21 |
| 16 | 201 | 211 | 207 | 1000 | 0.5 | 0.6 | 84 | 54 | 0.1 | 0.67 | 3.02 | 3.47 |
| 5 | 150 | 166 | 169 | 1000 | 2.4 | 0.6 | 75 | 57 | 0.0075 | 0.04 | 0.18 | 0.21 |
| 26 | 206 | 209 | 203 | 1000 | 2.44 | 0.57 | 97 | 51 | 0.32 | 1.99 | 8.91 | 10.34 |
| 27 | 155 | 170 | 171 | 1000 | 2.46 | 1.8 | 32 | 24 | 0.0075 | 0.04 | 0.42 | 0.50 |
| 9 | 171 | 212 | 208 | 1000 | 2.5 | 1.8 | 97 | 60 | 0.2 | 1.55 | 0.42 | 6.85 |

FIGURE 5

Table 9.

| Exp | Temperature | | | H₂ Press. | NaOH | LHSV | Conversion | PG Yield | Butanediols (g/100g) | | | 2,3-BDO (g/100 g) | Total BDO (g/100 g) |
|---|---|---|---|---|---|---|---|---|---|---|---|---|---|
| # | Top | Mid | Bottom | (psi) | (%) ʷ/w | | (%) | (%) | 1-2 BDO | 2-3 BDO | | on PG basis | on PG basis |
| 25 | 167 | 170 | 168 | 1000 | 0.46 | 0.54 | 28 | 21 | 0.0075 | 0.01 | | 0.12 | 0.21 |
| 6 | 150 | 166 | 169 | 1000 | 0.5 | 2 | 14 | 10 | 0.0075 | 0.0075 | | 0.19 | 0.38 |
| 16 | 201 | 211 | 207 | 1000 | 0.5 | 0.6 | 84 | 54 | 0.1 | 0.67 | | 3.02 | 3.47 |
| 21 | 180 | 205 | 210 | 1000 | 0.5 | 1.9 | 47 | 33 | 0.05 | 0.36 | | 2.68 | 3.05 |
| 5 | 150 | 166 | 169 | 1000 | 2.4 | 0.6 | 75 | 57 | 0.0075 | 0.04 | | 0.18 | 0.21 |
| 27 | 155 | 170 | 170 | 1000 | 2.46 | 1.8 | 32 | 24 | 0.0075 | 0.04 | | 0.42 | 0.50 |
| 26 | 206 | 209 | 203 | 1000 | 2.44 | 0.57 | 97 | 51 | 0.32 | 1.99 | | 8.91 | 10.34 |
| 9 | 171 | 212 | 208 | 1000 | 2.5 | 1.8 | 97 | 60 | 0.2 | 1.55 | | 6.07 | 6.85 |

FIGURE 6

Table 10.

| Exp | Temperature | | | H₂ Press. | NaOH | LHSV | Convrsn | PG Yield | Butanediols (g/100g) | | 2,3-BDO (g/100 g) | | Total BDO (g/100 g) |
|---|---|---|---|---|---|---|---|---|---|---|---|---|---|
| # | Top | Mid | Bottom | (psi) | (%) w/w | | (%) | (%) | on PG basis | on PG basis | on PG basis | on PG basis | on PG basis |
| 283 | 176 | 193 | 176 | 1600 | 0.8 | 1.01 | 83.7 | 56 | 0.02 | 0.03 | 0.13 | | 0.22 |
| 284 | 188 | 204 | 188 | 1600 | 0.8 | 1 | 92.4 | 61 | 0.04 | 0.08 | 0.32 | | 0.48 |
| 285 | 195 | 216 | 195 | 1600 | 0.8 | 1.02 | 97.5 | 60.1 | 0.05 | 0.11 | 0.45 | | 0.65 |

FIGURE 7

Table 11

| Run | Temp (C) Top | Temp (C) Mid | Temp (C) Bot | Pressure (psig) | NaOH (%) | LHSV | Glycerol Conversion (%) | PG Selectivity (Mole %) | 1-2 BuDO g/100g | 2-3 BuDO g/100g | Total BDOs (g/100g) | Total BDOs (g/100g) on PG basis |
|---|---|---|---|---|---|---|---|---|---|---|---|---|
| D16-M-423-01 | 175 | 191 | 209 | 1850 | 0.65 | 9.95 | 52.27 | 79.78 | 0.08 | 0.57 | 0.65 | 4.65 |
| D16-M-423-02 | 173 | 189 | 205 | 1850 | 0.65 | 9.87 | 49.31 | 81.08 | 0.08 | 0.49 | 0.57 | 4.25 |
| D16-M-423-03 | 173 | 191 | 207 | 1850 | 0.66 | 9.81 | 48.97 | 82.45 | 0.07 | 0.47 | 0.54 | 4.06 |
| D16-M-423-04 | 171 | 191 | 208 | 1850 | 0.66 | 9.86 | 50.34 | 77.52 | 0.07 | 0.47 | 0.54 | 4.05 |
| D16-M-423-05 | 172 | 191 | 208 | 1850 | 0.66 | 9.86 | 49.33 | 80.79 | 0.07 | 0.49 | 0.56 | 4.16 |
| D16-M-423-06 | 172 | 191 | 208 | 1850 | 0.66 | 9.90 | 49.79 | 79.73 | 0.06 | 0.43 | 0.49 | 3.68 |
| D16-M-423-07 | 169 | 193 | 212 | 1850 | 0.64 | 9.98 | 41.21 | 76.33 | 0.05 | 0.37 | 0.42 | 3.91 |
| D16-M-424-01 | 172 | 191 | 192 | 1850 | 0.63 | 9.78 | 43.17 | 76.18 | 0.06 | 0.35 | 0.41 | 3.63 |
| D16-M-424-02 | 167 | 192 | 207 | 1850 | 0.64 | 9.95 | 38.68 | 90.76 | 0.05 | 0.34 | 0.39 | 3.43 |
| D16-M-424-03 | 154 | 182 | 191 | 1850 | 0.63 | 9.95 | 22.33 | 95.76 | 0.00 | 0.23 | 0.23 | 3.31 |
| D16-M-424-04 | 159 | 179 | 194 | 1850 | 0.65 | 9.92 | 18.71 | 96.79 | 0.00 | 0.16 | 0.16 | 2.68 |
| D16-M-424-05 | 159 | 179 | 193 | 1850 | 0.64 | 9.99 | 26.07 | 90.05 | 0.04 | 0.20 | 0.24 | 3.10 |
| D16-M-425-01 | 174 | 186 | 200 | 1850 | 0.64 | 9.91 | 43.82 | 84.79 | 0.06 | 0.40 | 0.46 | 3.77 |
| D16-M-425-02 | 174 | 186 | 200 | 1850 | 0.65 | 9.90 | 45.70 | 79.24 | 0.06 | 0.40 | 0.46 | 3.75 |
| D16-M-425-03 | 175 | 186 | 200 | 1850 | 0.63 | 9.93 | 44.41 | 83.37 | 0.07 | 0.36 | 0.43 | 3.50 |
| D16-M-425-04 | 173 | 180 | 190 | 1850 | 0.66 | 9.84 | 32.21 | 83.35 | 0.03 | 0.24 | 0.27 | 3.01 |
| D16-M-425-05 | 172 | 179 | 191 | 1850 | 0.67 | 9.88 | 33.21 | 83.29 | 0.03 | 0.24 | 0.27 | 2.93 |
| D16-M-425-06 | 173 | 180 | 191 | 1850 | 0.66 | 9.96 | 33.76 | 82.19 | 0.03 | 0.21 | 0.24 | 2.57 |

FIGURE 8

Table 12

| I.D. | Conversion Wt % | PG Yield Wt % | 2,3-BDO PG Basis | Selctvty Mole % | Temp (°C) | Press psig | NaOH Wt % | LHSV |
|---|---|---|---|---|---|---|---|---|
| S-377 | 95 | 69 | 1.6 | 88 | 198 | 1200 | 0.68 | 1.08 |
| S-395 | 93 | 70 | 1.0 | 91 | 200 | 1600 | 0.69 | 1.04 |
| S-396 | 91 | 69 | 0.5 | 92 | 200 | 1800 | 0.70 | 1.03 |
| S-397 | 90 | 68 | 0.4 | 92 | 199 | 2000 | 0.69 | 1.01 |

FIGURE 9

HYDROGENOLYSIS OF GLYCEROL AND PRODUCTS PRODUCED THEREFROM

CROSS-REFERENCE TO RELATED APPLICATIONS

The application claims the priority benefit under 35 U.S.C. §119(e) to U.S. Provisional Patent Application No. 60/853,574, filed Oct. 23, 2006, the contents of the entirety of which is incorporated by this reference.

TECHNICAL FIELD

This invention relates to processes for producing polyhydric glycerol derivatives, as well as compositions obtained therefrom.

BACKGROUND

Catalytic hydrogenolysis (hydrocracking) of polyol is a process whereby polyols such as sugars, glycerol and glycols are reacted with hydrogen to produce other polyols. The polyols so produced often comprise a mixture of several polyols having a lower average molecular weight than the starting material. The impurity of the polyol product mixture (derivatives) presents a problem for sale and use of the product.

The conversion of polyols such as sugars and glycerol to polyhydric alcohols such as propylene glycol and ethylene glycol by hydrogenolysis or by hydrocracking results in formation of not only these alcohols, but several other unwanted products, such as 1,2-butanediol, 1,3-butanediol, 1,4-butanediol, 2,3-butanediol and 2,4-pentanediol. These products are recovered with the propylene glycol and ethylene glycol. Due to the similarity in boiling points, these diols are very difficult to separate from propylene glycol by distillation. For instance, in hydrocracking of higher carbohydrates such as sorbitol to produce propylene glycol, typically 3-5% by weight of 2,3-butanediol is produced in addition to 1,2-butanediol, ethylene glycol and 1,3-butanediol. Table 2 provides a list of polyols produced by hydrocracking of sorbitol as described in U.S. Pat. No. 4,935,102, which is incorporated herein by reference in its entirety. The boiling points of these components as shown in Table 1 are very close to one another such that in a rectification column, either under atmospheric pressure, reduced pressure or at an elevated pressure, the separation of substantially pure propylene glycol is difficult to attain.

TABLE 1

Polyols produced by Hydrocracking of Sorbitol (U.S. Pat. No. 4,935,102)

| Compound | Weight Percent | Boiling Point, ° C. |
|---|---|---|
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerol | 38.8 | 290 |
| 1,2,4-Butanetriol | 4.8 | 190/18 mm |
| | 100.00 | |

The differences in volatility of propylene glycol compared to 2,3-butanediol and 1,2 butanediol are very small. As shown in Tables 2 and 3, for separation of these compounds from a mixture by distillation, the number of plates required to achieve 99% purity is very large; thus very tall distillation columns (55 trays for 2,3-Butanediol and 88 trays for 1,2-Butanediol) and high energy inputs are required.

TABLE 2

Theoretical and Actual Plates Required vs. Relative volatility for Propylene Glycol - 2,3-Butanediol Separation.

| Relative Volatility | Theoretical Plates | Actual Plates, 75% Efficiency |
|---|---|---|
| 1.25 | 41 | 55 |
| 1.35 | 31 | 42 |
| 1.45 | 25 | 34 |
| 1.50 | 23 | 31 |
| 1.70 | 18 | 24 |

TABLE 3

Theoretical and Actual Plates Required vs. Relative volatility for Propylene Glycol - 1,2-Butanediol Separation.

| Relative Volatility | Theoretical Plates | Actual Plates, 75% Efficiency |
|---|---|---|
| 1.15 | 66 | 88 |
| 1.5 | 23 | 31 |
| 2.0 | 14 | 19 |
| 3.0 | 9 | 12 |
| 3.5 | 8 | 11 |

The processes involved in the hydrogenolysis of glycerol may be carried out by any of the known routes. These include heterogeneous metal catalysts, such as those described in U.S. Pat. No. 6,479,713, PCT patent application WO 2005/051874, US patent application 2005/0244312 or referred to in Catalysis Communications 6 (2005) 645-649 or Journal of Catalysis 240 (2006) 213-221, each of the contents of the entirety of which are incorporated herein by this reference. The processes also include homogenous catalysts as referred to in Hydrocarbon Processing (February 2006) pp 87-92, the contents of the entirety of which is incorporated by this reference. Other processes include U.S. Pat. Nos. 4,401,823; 5,354,914; 6,291,725 and 6,479,713, each of the contents of the entirety of which are incorporated by this reference. U.S. Pat. No. 6,479,713 describes a process including: substrates such as glycerol, sorbitol, xylitol, lactic acid, and arabinitol which are subjected to hydrogenolysis over a catalyst comprising Re—Ni supported on carbon at 230° C. and 1300 psi hydrogen pressure to give two- and three-carbon glycols similar to those obtained from petrochemical-based feed stocks. In one example, after 1 hour, 25.3% glycerol conversion was achieved with 72.3% selectivity to propylene glycol.

The catalytic hydrogenolysis process may also involves a Nickel-on-alumina catalyst (C46-8-03 RS) obtained from United Catalysts Inc. (now Sud Chemie). This catalyst had the characteristics outlined in Table 4.

TABLE 4

| C46-8-03 RS Hydrogenolysis catalyst characteristics | |
|---|---|
| Nickel (wt %) | 48.9 |
| SiO2 (wt %) | 4.59 |
| Al2O3 (wt %) | 30.3 |
| Shape | Cylindrical |
| Average length (mm) | 5.1 |
| Average crush strength (lbs/mm) | 1.8 |
| Reduction (%) | 43 |

The composition of the hydrogenolysis product mixture may be dependent on certain conditions, such as, for example, the particular bio-derived polyol feedstock or the hydrogenolysis process used. In a process (U.S. Pat. No. 6,479,713), mixed polyols were synthesized by feeding a 25% sorbitol solution into a reactor containing an alumina-based massive nickel catalyst (cylinder shaped) promoted with sodium hydroxide or sodium carbonate to 1% sodium. Over a period of 72 days, the feed (specific gravity, 1.1 g/mL, pH~11.5) was fed into the reactor held at 180-250° C. under 200-1800 psi pressure. A representative product contained 47% propylene glycol, 20% ethylene glycol, 21% glycerol, and the remainder was mixed diols.

Hydrogenolysis is a fixed bed catalytic process that uses hydrogen from 1000-2000 psi, often at temperatures of 180-250° C. and typically is under alkaline conditions. U.S. Pat. No. 6,479,713 describes a process where a nickel-rhenium-on-carbon catalyst was loaded into a 300-mL semi-batch Parr reactor and purged with nitrogen. The catalyst was activated by adding hydrogen at 500 psi and heating to 280° C. for 16 h with stirring. The reactor was cooled, the hydrogen removed, and 105.5 g of an aqueous solution of sorbitol (25%) and KOH (0.94%) was added. The reactor was pressurized to 600 psi with hydrogen and heated; when the temperature reached 220° C., the pressure was raised to 1200 psi. The reaction was run for 4 h. Depending on the catalyst composition, sorbitol conversions ranged from 48.8 to 62.8%. In most cases, the major products were glycerol, propylene glycol, and ethylene glycol. Other feed stocks tested included xylitol, arabinitol, lactic acid, and glycerol.

In U.S. Pat. No. 6,479,713, alditols (such as a 15-40 wt % sorbitol solution in water) are catalytically hydrocracked in a fixed bed catalytic reaction process using an active nickel catalyst to produce at least about 30 W % conversion to glycerol and glycol products. The feed stream pH is controlled to between 7 and 14 by adding an alkali material such as calcium hydroxide or a strong base such as sodium hydroxide to prevent damage to the catalyst. Useful prior art reaction conditions are 400-500° F., 1200-2000 psig hydrogen partial pressure, and a liquid hourly space velocity of 1.5 to 3.0. To maintain desired catalyst activity and product yields, the catalyst is regenerated to provide catalyst age within the range of 20-200 hours. The reaction products are separated in distillation steps at successively lower pressures, and unconverted alditol feed is recycled to the reaction zone for further hydrogenolysis to produce 80-95 W % glycerol product. Sorbitol conversion is maintained at between about 30-70 W % by catalyst regeneration following 20 to 200 hours use, comprising washing to remove deposits and heating with hydrogen at 500-600° F. temperature. Countercurrent flow of feed and hydrogen in the reaction zone can be used if desired, particularly for achieving higher conversion of alditol feed to glycerol products.

SUMMARY OF THE INVENTION

In one embodiment, a composition comprises a biobased propylene glycol and a weight/weight ratio of polyhydric alcohols other than propylene glycol to the biobased propylene glycol of 0.5% or less.

In another embodiment, a composition includes a biobased propylene glycol and polyhydric alcohols other than propylene glycol. In the composition, a ratio of the biobased propylene glycol to the polyhydric alcohols is between 100:1 and 1000:1

In a further embodiment, a system for producing biobased propylene glycol comprises a conduit comprising a biobased glycerol containing solution at a concentration of at least 30% glycerol and a reactor. The reactor comprises a solid catalyst. The system further comprises a second conduit comprising a biobased propylene glycol and polyhydric alcohols other than propylene glycol, wherein a weight/weight ratio of the polyhydric alcohols to the biobased propylene glycol is 0.5% or less.

In yet an additional embodiment, a process for producing biobased propylene glycol comprises placing a biobased glycerol containing solution at a concentration of at least 30% glycerol by weight and hydrogen in contact with a solid catalyst such that the biobased propylene glycol is formed.

In yet another embodiment, a composition comprises polyhydric alcohols obtained from a biobased feed stock. The polyhydric alcohols comprise propylene glycol in an amount of at least 997 g/kg on a dry weight basis and 1,2-butanediol, 1,3-butanediol, 1,4-butanediol, 2,3-butanediol, 2,4-pentanediol, ethylene glycol or any combinations thereof. The 1,2-butanediol, the 1,3-butanediol, the 1,4-butanediol, the 2,3-butanediol, the 2,4-pentanediol, the ethylene glycol or any of the combinations thereof are present at a concentration of less than 0.5% of the propylene glycol concentration on dry weight basis

DESCRIPTION OF THE DRAWINGS

FIG. 2A is Table 5A.
FIG. 2b is Table 5B.
FIG. 3 is Table 6.
FIG. 4 is Table 7.
FIG. 5 is Table 8.
FIG. 6 is Table 9.
FIG. 7 is Table 10.
FIG. 8 is Table 11.
FIG. 9 is Table 12.

DETAILED DESCRIPTION OF THE INVENTION

Figure 1:
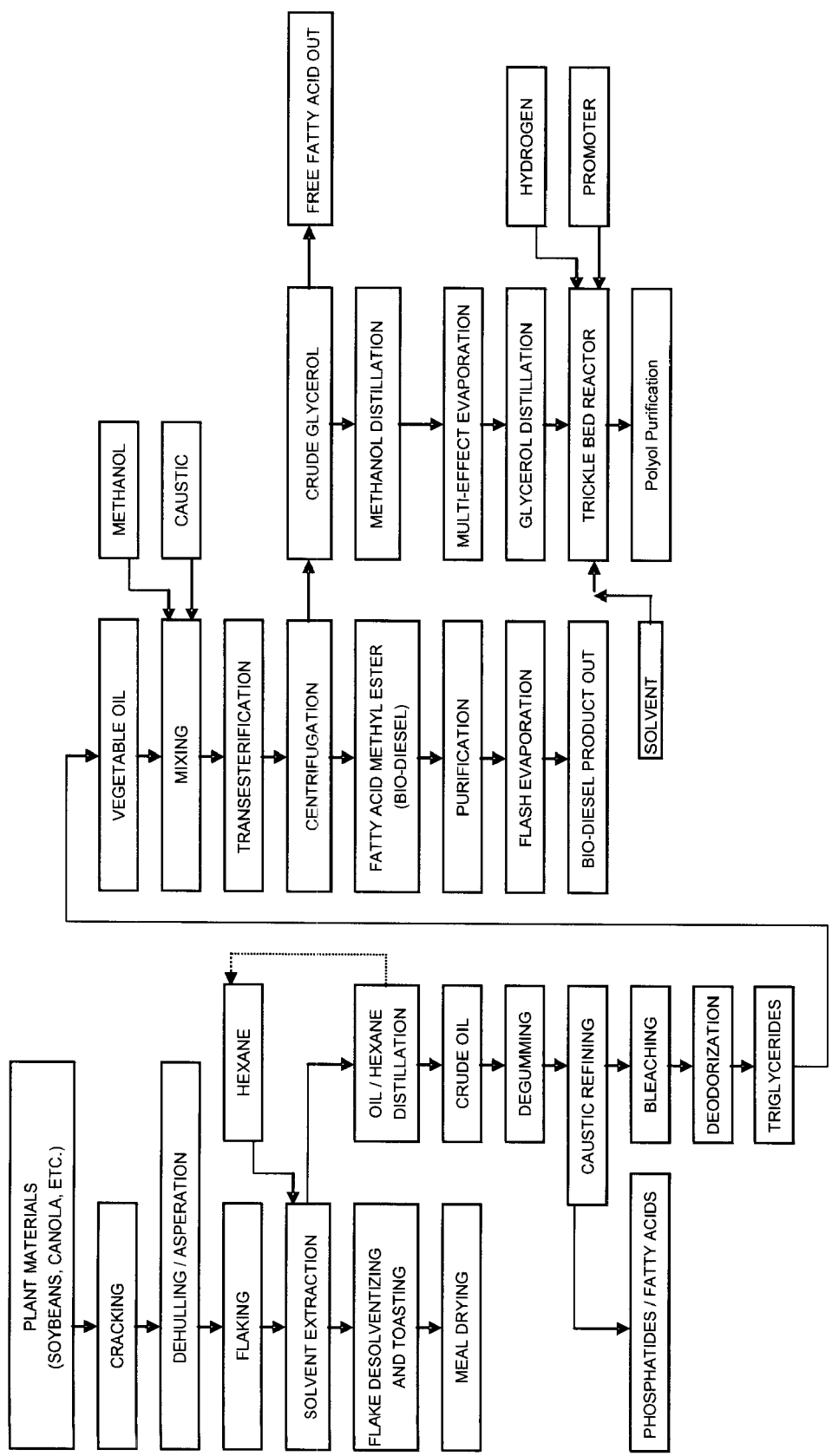
FIG. 1 is a schematic block flow diagram illustrating one embodiment of a process for producing value added biobased products such as propylene glycol and ethylene glycol from a bio-renewable feed stock such as a plant oil seed.
Figure 10:
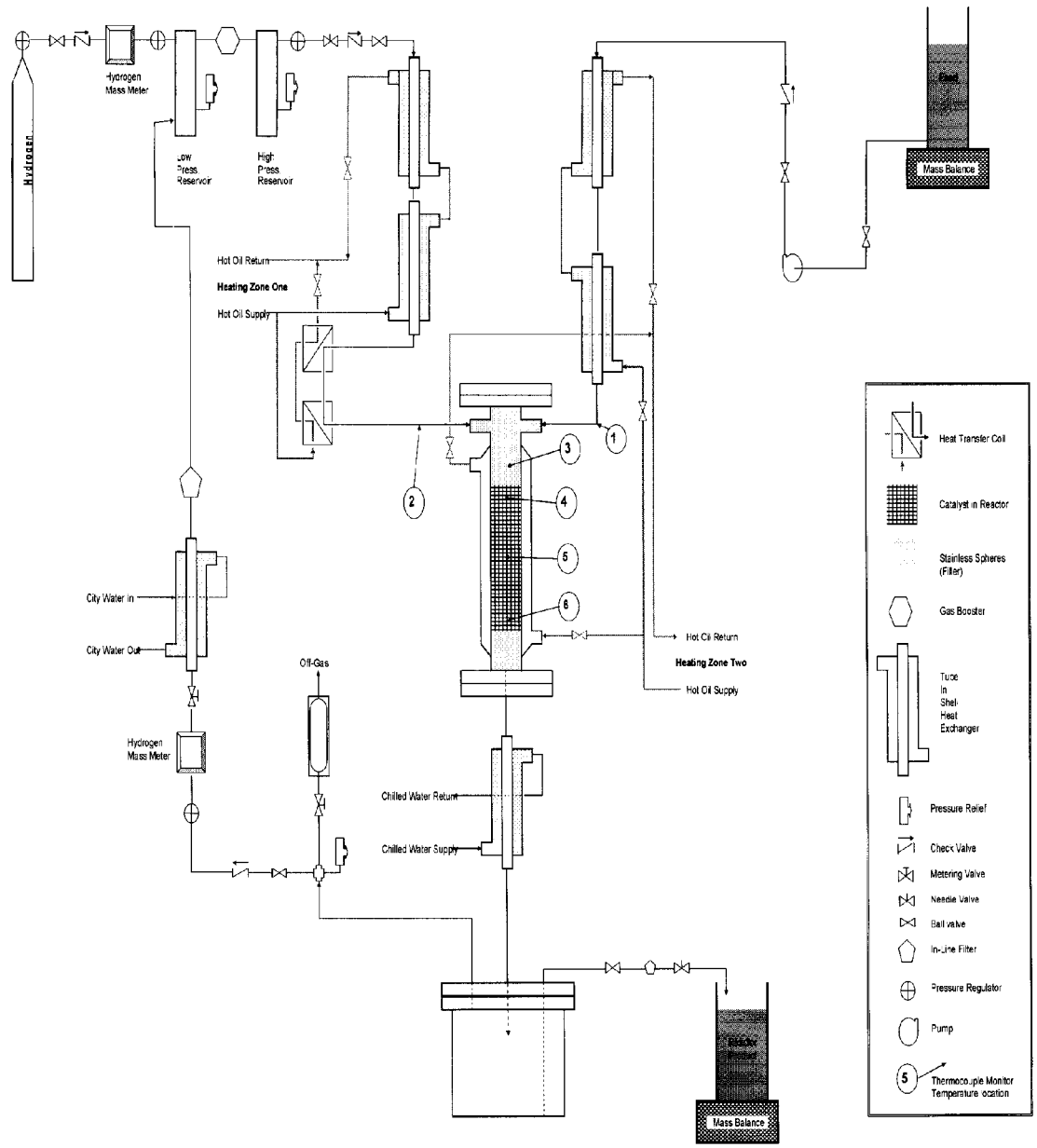
FIG. 10 is one embodiment of a system for producing biobased propylene glycol.

The processes of the present disclosure provide methods for conversion of glycerol to useful derivatives and overcome the problems in current technologies by producing value-added products including, but not limited to, propylene glycol and ethylene glycol by hydrogenation of glycerol feed stocks.

In one embodiment, the present disclosure provides processes for conversion of crude glycerol into substantially pure propylene glycol.

In one embodiment, the present invention provides methods for hydrogenolysis of polyols which maximize the selectivity of the reaction towards formation of propylene glycol and minimizes the formation of other polyols. In one embodiment, the present invention discloses processes for hydrogenolysis of glycerol which maximizes the selectivity of the reaction towards formation of propylene glycol and minimizes the formation of other polyols. In another embodiment, reaction conditions are provided for different catalysts that can be applied to any hydrogenolysis process for conversion of glycerol to propylene glycol. In one embodiment, selective formation of propylene glycol is obtained with little or negligible formation of other polyols that are difficult to separate by distillation, such as 1,2-butanediol and 2,3-butanediol.

In one embodiment, a process is provided for hydrogenolysis of glycerol comprising placing glycerol in contact with hydrogen and a solid catalyst at a liquid hourly space velocity of 0.5 $hr^{-1}$ to 10.0 $hr^{-1}$ to minimize formation of butanediols.

In another embodiment, the process for hydrogenolysis of glycerol while minimizing formation of butanediols comprises adding a base.

In another embodiment, the process for hydrogenolysis of glycerol while minimizing formation of butanediols comprises adding a base selected from the group consisting of alkali metal hydroxides, alkoxides and basic salts and alkaline earth metal oxides, alkoxides, hydroxides and basic salts.

In another embodiment, the process for hydrogenolysis of glycerol while minimizing formation of butanediols comprises adding a base in an amount from about 0.01 to about 2.5 weight percent of the glycerol solution.

In another embodiment, the process for hydrogenolysis of glycerol while minimizing formation of butanediols comprises adding a base at a level to maximize selective formation of propylene glycol over other polyhydric alcohols.

In another embodiment, the process for hydrogenolysis of glycerol while minimizing formation of butanediols comprises adding a strong base is added at 1-1.9 weight percent base.

In another embodiment, the process for hydrogenolysis of glycerol while minimizing formation of butanediols comprises operating at a reaction temperature of 178-205 degrees Centigrade.

In another embodiment, the process for hydrogenolysis of glycerol while minimizing formation of butanediols comprises operating at a reaction temperature of 176-193 degrees Centigrade.

In another embodiment, the process for hydrogenolysis of glycerol while minimizing formation of butanediols comprises operating at a Liquid Hourly Space Velocity of 1.5-2.3 $hr^{-1}$.

In another embodiment, the process for hydrogenolysis of glycerol while minimizing formation of butanediols comprises hydrogenolysis of glycerol from fats or oils, comprising purifying a crude glycerol solution, bringing the glycerol solution in contact with hydrogen in a solution containing a solid catalyst at a temperature between 100-220° C. and a Liquid Hourly space velocity of 0.5 $hr^{-1}$ to 2.5 $hr^{-1}$ to produce a stream of polyhydric glycols and fractionating the glycols stream.

In another embodiment, the process for hydrogenolysis of glycerol while minimizing formation of butanediols comprises adding the strong base at a level to minimize formation of 1,3-butanediol and 2,3-butanediol.

In another embodiment, the process for hydrogenolysis of glycerol while minimizing formation of butanediols comprises adding the strong base at a level to maximize selective formation of propylene glycol over other polyhydric alcohols.

In another embodiment, the process for hydrogenolysis of glycerol while minimizing formation of butanediols comprises mixing a glycerol containing material with a base, to produce a hydrogenolysis precursor mixture, subjecting the hydrogenolysis precursor mixture to a condition that allows propylene glycol to form, wherein the condition is selected from the group consisting of liquid hourly space velocity, temperature, pressure, the presence of a catalyst and any combination thereof, wherein the propylene glycol is isolated and other polyhydric alcohols are removed from the propylene glycol.

In a further embodiment, the process for hydrogenolysis of glycerol, while minimizing formation of butanediols, comprises the use of a the glycerol containing material that is selected from the group consisting of products of bio-diesel processing, petroleum processing, soap processing, fats processing, and mixtures of any thereof.

In a further embodiment, the process for hydrogenolysis of glycerol, while minimizing formation of butanediols, comprising associating indicia with the propylene glycol to indicate that the propylene glycol has a reduced content of other polyhydric alcohols.

According to certain embodiments, the bio-derived polyol feedstock can be obtained by subjecting sugars or carbohydrates to hydrogenolysis (also called catalytic cracking). In one embodiment, sorbitol may be subjected to hydrogenolysis to provide a mixture comprising bio based polyols, as described herein (see, e.g. "Hydrogenolysis of sorbitol," Clark, I., *J. Ind. Eng. Chem.* (Washington, D.C.) (1958), 50, 1125-6, the disclosure of which is incorporated by reference herein in its entirety). According to other embodiments, other polysaccharides and polyols suitable for hydrogenolysis include, but are not limited to, glucose (dextrose), sorbitol, mannitol, sucrose, lactose, maltose, alpha-methyl-d-glucoside, pentaacetylglucose, gluconic lactone and any combination thereof (see, e.g. "Hydrogenolysis of sugars," Zartman, W. and Adkins, H., *J. Amer. Chem. Soc.* (1933) 55, 4559-63, the disclosure of which is incorporated by reference herein in its entirety).

According to other embodiments, the biobased polyol feedstock may be obtained as mixed polyols. Natural fibers may be hydrolyzed (producing a hydrolyzate) to provide bio-derived polyol feedstock, such as mixtures of polyols. Fibers suitable for this purpose include, but are not limited to, corn fiber from corn wet mills, dry corn gluten feed which contains corn fiber from wet mills, wet corn gluten feed from wet corn mills that do not run dryers, distiller dry grains solubles (DDGS) and Distiller's Grain Solubles (DGS) from dry corn mills, canola hulls, rapeseed hulls, peanut shells, soybean hulls, cottonseed hulls, cocoa hulls, barley hulls, oat hulls, wheat straw, corn stover, rice hulls, starch streams from wheat processing, fiber streams from corn mesa plants, edible bean molasses, edible bean fiber, and mixtures of any thereof. Hydrolyzates of natural fibers, such as corn fiber, may be enriched in bio-derived polyol feedstock suitable for use as a feedstock in the hydrogenation reaction described herein, including, but not limited to, arabinose, xylose, sucrose, maltose, isomaltose, fructose, mannose, galactose, glucose, and mixtures of any thereof.

According to other embodiments, the bio-derived polyol feedstock obtained from hydrolyzed fibers may be subjected to fermentation. The fermentation process may provide modified bio-derived polyol feed stocks, or may alter the amounts of residues of polysaccharides or polyols obtained from hydrolyzed fibers. After fermentation, a fermentation broth may be obtained and residues of polysaccharides or polyols can be recovered and/or concentrated from the fermentation broth to provide a bio-derived polyol feedstock suitable for hydrogenolysis, as described herein.

According to certain embodiments, the hydrogenolysis product may comprise a mixture of propylene glycol and ethylene glycol, along with minor amounts of one or more of methanol, 2-propanol, glycerol, lactic acid, glyceric acid, sodium lactate, and sodium glycerate. Several butanediols (BDO) such 1,2-butanediol, 1,3-butanediol, 1,4-butanediol, and 2,3-butanediol are produced in addition to 2,4-Pentanediol (2,4-PeDO).

In various embodiments, the hydrogenolysis product of the present invention comprising the biobased propylene glycol may be used in a composition including, but not limited to, a deicer, an antifreeze, a resin, a laundry detergent, a soap, a personal care product, a cosmetic product, a pharmaceutical product, or as a food ingredient in a foodstuff or beverage.

Hydrogenolysis of bio-derived polyol feed stocks includes, but is not limited to, polyol feed stocks derived from biological or botanical sources. For example, bio-derived polyols suitable for use according to various embodiments of the present disclosure include, but are not limited to: saccharides, such as, but not limited to, biologically derived (bio-derived) polyols including monosaccharides including dioses, such as glycolaldehyde; trioses, such as glyceraldehyde and dihydroxyacetone; tetroeses, such as erythrose and threose; aldopentoses such as arabinose, lyxose, ribose, deoxyribose, xylose; keto-pentoses, such as ribulose and xylulose; aldohexoses such as allose, altrose, galactose, glucose (dextrose), gulose, idose, mannose, talose; keto-hexoses, such as fructose, psicose, sorbose, tagatose; heptoses, such as mannoheptulose and sedoheptulose; octoses, such as octolose and 2-keto-3-deoxy-manno-octonate; and nonoses, such as sialose; disaccharides including sucrose (table sugar, cane sugar, saccharose, or beet sugar) having glucose+fructose; lactose (milk sugar) having glucose+galactose; maltose (produced during the malting of barley) having glucose+glucose; trehalose is present in fungi and insects, and is glucose+glucose; cellobiose is a glucose+glucose disaccharide; oligosaccharides, such as raffinose (melitose), stachycose, and verbascose; sorbitol, glycerol, sorbitan, isosorbide, hydroxymethyl furfural, polyglycerols, plant fiber hydrolyzates, fermentation products from plant fiber hydrolyzates, and various mixtures of any thereof.

As used herein, the term polyhydric alcohols may refer to a hydrogenated form of a carbohydrate, where the carbonyl group (aldehyde or ketone) has been reduced to a primary or secondary hydroxyl group. The term may also be used to refer to glycerol, propylene glycol, ethylene glycol, sorbitol and/or BDO.

In one embodiment, the feedstock is glycerol. In an embodiment, the glycerol feed stock includes a diluent, such as water, or a non-aqueous solvent. Non-aqueous solvents that may be used include, but are not limited to, methanol, ethanol, ethylene glycol, propylene glycol, n-propanol and iso-propanol. Glycerol feed stocks are commercially available, or can be obtained as a byproduct of commercial biodiesel production. According to other embodiments, the bio-derived polyol feedstock may be a side product or co-product from the synthesis of bio-diesel or the saponification of vegetable oils and/or animal fats (i.e., triacylglycerols). For instance, the glycerol feed stocks may be obtained through fats and oils processing or generated as a byproduct in the manufacture of soaps. The feed stock may for example, be provided as glycerol byproduct of primary alcohol alcoholysis of a glyceride, such as a mono-, di- or tri glyceride. These glycerides may be obtained from refining edible and non-edible plant feed stocks including without limitation butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, tallow, animal fat, canola oil, castor oil, coconut oil, coriander oil, corn oil, cottonseed oil, hazelnut oil, hempseed oil, jatropha oil, linseed oil, mango kernel oil, meadowfoam oil, mustard oil, neat's foot oil, olive oil, palm oil, palm kernel oil, peanut oil, rapeseed oil, rice bran oil, safflower oil, sasanqua oil, shea butter, soybean oil, sunflower seed oil, tall oil, tsubaki oil, tung oil, vegetable oils, marine oils, menhaden oil, candlefish oil, cod-liver oil, orange roughy oil, pile herd oil, sardine oil, whale oils, herring oils, triglyceride, diglyceride, monoglyceride, triolein palm olein, palm stearin, palm kernel olein, palm kernel stearin, triglycerides of medium chain fatty acids, and derivatives, conjugated derivatives, genetically-modified derivatives and mixtures of any thereof.

Glycerol feed stocks are known to those of ordinary skill in the art and can be used either in pure or crude form. The purity of United States Pharmacopeia grade glycerol is greater than 99%. However, the purity of the glycerol having utility in the present invention may be between 10-99% by weight. The glycerol may also contain other constituents such as water, triglycerides, free fatty acids, soap stock, salt, and unsaponifiable matter. In one embodiment, the feed stocks may comprise 20-80% by weight of glycerol.

Catalysts for the present hydrogenolysis processes are solid or heterogeneous catalysis. The catalysts may include those known in the art or as described herein. The catalysts are provided with a large surface area support material that prevents degradation under the reaction conditions. These supports may include, but are not limited to, carbon, alumina, titania and zirconia, silica, or a combination thereof. These supports can also be prepared in mixed or layered materials such as mixed with catalyst materials. The hydrogenolysis catalyst used in the reaction may be a primary heterogeneous catalyst selected from the group consisting of palladium, rhenium, nickel, rhodium, copper, zinc, chromium or any combinations thereof. In one embodiment, a secondary catalyst is used in addition to the primary metal catalyst. Secondary catalysts may comprise additional metals, including without limitation nickel, palladium, ruthenium, cobalt, silver, gold, rhenium, platinum, iridium, osmium, copper and any combination thereof. In one embodiment, combinations of metals such as nickel/rhenium, copper/rhenium, and cobalt/rhenium may be employed. Alternatively, the catalyst may be a homogenous catalyst, such as an ionic liquid or an osmonium salt which remains liquid under the reaction conditions employed.

Catalytic hydrogenolysis can further comprise utilization of an added base. Assuming a neutral starting pH of a polyol feedstock, such as sorbitol or glycerol, of from about pH 5 to about pH 8, an appropriate pH for catalytic hydrogenolysis can be achieved by, for example, an addition an alkali, such as sodium hydroxide, to a final concentration of from about 0% to about 10% by weight, or from about 0.5% to about 2% by weight, relative to the weight of the final solution. In some cases, the added strong alkali base has been referred to as a "promoter". In an embodiment, the selectivity of the catalyst and yield of propylene glycol (PG) can be improved by treating the reactant mixture to render the pH value neutral or alkali prior to or during the hydrogenolysis reaction, as well as carrying out the reaction under alkaline conditions. During the reaction, organic acids are formed which neutralize the alkali added to the reaction. As the reaction proceeds, the pH is reduced, causing concomitant reduction in the selectivity of the catalyst. Methods are provided in the present disclosure to ensure that the reaction is carried out in sufficient alkalinity to ameliorate this problem. In one embodiment, the reaction is conducted under alkali conditions, such as at a pH 8 to 14, or at a pH of 10 to 13. These pH values may be obtained by adding an alkali, such as a strong base such as sodium hydroxide. In embodiments, the sodium hydroxide could be added to a level of 0.2 to 0.7%.

The temperature used in the hydrogenolysis reaction may range from 150° C. to 300° C. while the pressure is between 500 psi and 2000 psi, or 1000 psi to 1600 psi. The reaction time for the hydrogenolysis reaction is defined by the term "weight hourly space velocity" (WHSV) which is the weight of reactant per unit weight of catalyst per hour. Alternatively, the term "liquid hourly space velocity" (LHSV) may also be used, and is volume of reactant per unit volume of catalyst per hour. In an embodiment, a value for HSV is 1.8, which can be modified suitably to meet reactor design specifications using techniques well known to those in the art.

The compositions and methods disclosed herein are not limited to any particular hydrogenolysis procedures, reagents, or catalysts. Rather, the compositions and methods described herein may incorporate hydrogenolysis products from any known method.

Hydrogenolysis of a bio-derived polyol feedstock such as, for example, a bio-derived polyol feed stock as described herein, results in a hydrogenolysis product. According to certain embodiments of the present disclosure, the hydrogenolysis product may comprise a mixture of propylene glycol and ethylene glycol containing minor amounts of one or more of methanol, 2-propanol, glycerol, lactic acid, glyceric acid, sodium lactate, sodium glycerate, and combinations of any thereof. According to certain embodiments, the hydrogenolysis product may comprise 0.1% to 99.9% by weight of propylene glycol, 0.1% to 99.9% by weight of ethylene glycol, 0.1% to 99.9% by weight of methanol, 0.10% to 99.9% by weight of 2-propanol, 0.1% to 99.9% by weight of glycerol, 0.1% to 99.9% by weight of lactic acid, 0.1% to 99.9% by weight of glyceric acid, 0.1% to 99.9% by weight of sodium lactate, and 0.1% to 99.9% by weight of sodium glycerate.

FRISA has established certification requirements for determining bio-based content. These methods require the measurement of variations in isotopic abundance between bio-based products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-based products compared to petroleum products. Bio-based content of a product may be verified by ASTM International Radioisotope Standard Method D 6866. ASTM International Radioisotope Standard Method D 6866 determines bio-based content of a material based on the amount of bio-based carbon in the material or product as a percent of the weight (mass) of the total organic carbon in the material or product. Bio-derived and bio-based products will have a carbon isotope ratio characteristic of a biologically derived composition.

Biology offers an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. As the supply of easily extracted petrochemicals continues to be depleted, the economics of petrochemical production will likely force the cost of the petrochemicals and petroleum derived products to higher prices compared to bio-based products. In addition, companies may benefit from the marketing advantages associated with bio-derived products from renewable resources in the view of a public becoming more concerned with the supply of petrochemicals.

Propylene glycol produced by the embodiments described herein is referred to as "bio-based" propylene glycol. Propylene glycol produced as such finds many uses. Some of these include, but are not limited to, use as a solvent for aromatics in the flavor-concentrate industry; a wetting agent for natural gums; an ingredient in the compounding of citrus and other emulsified flavors; a solvent in elixirs and pharmaceutical preparations; a solvent and coupling agent in the formulation of sunscreen lotion shampoos, shaving creams and other similar products; an emulsifier in cosmetic and pharmaceutical creams; an ingredient for low-temperature heat-transfer fluids, involving indirect food contacts, such as brewing and dairy uses, as well as refrigerated grocery display cases; a very effective humectant, preservative, and stabilizer in semi-moist pet food, bakery goods, food flavorings and salad dressings; use as a dust suppression agent; solvents and compatibilizers for the many dyes, resins and inks used in modern high-speed printing presses; surface lubricant in metal part manufacture; as a raw material for dipropylene glycol phthalate; a plasticizer for polyvinyl chloride (PVC) resins; for use in the natural gas processing industry; and to provide freeze-thaw protection in various wax products to help prevent damaged caused by freezing. Propylene glycol is also used as the starting material for the synthesis of propylene glycol esters with sorbitol and/or fatty acids. Such uses are not limited or all inclusive and may be readily developed by those skilled in the art.

Various embodiments of the present disclosure relate to a bio-based propylene glycol and ethylene glycol. The products produced by the processes of the present invention produced by the hydrogenolysis of bio-derived polyols and the products produced therefrom may be differentiated from petroleum derived products, for example, by their carbon isotope ratios using ASTM International Radioisotope Standard Method D 6866. Products produced from the product mixture of the hydrogenolysis product from a bio-derived polyol feedstock may have a bio-based carbon isotope ratio ranging from 50% to 100. As used herein the term "bio-based carbon isotope ratio" includes a composition or a component of a composition having a carbon isotope ratio, as determined, for example, by ASTM International Radioisotope Standard Method D 6866, the disclosure of which is incorporated by reference herein in its entirety, that is indicative of a composition including, in whole or in significant part, of biological products or renewable agricultural materials (including plant, animal and marine materials) or forestry materials [Method ASTM 6866].

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

Example 1

A series of studies were conducted in a 2000 ml high-pressure Stainless Steel 316 reactor. As described in FIG. 1, a solid catalyst similar to the "G" catalyst disclosed in U.S. Pat. No. 6,479,713 or the "HC-1" catalyst available from Süd Chemie (Louisville, Ky.) was loaded in the reactor to a final volume of 1000 ml of catalyst. The reactor was jacketed with a hot oil bath to provide for the elevated temperature for reactions and the feed and hydrogen lines were also preheated to the reactor temperature. A solution of a bio-based, substantially pure, 40% USP grade glycerol was fed through the catalyst bed at LHSV ranging from 0.5 $hr^{-1}$ to 2.5 $hr^{-1}$. Hydrogen was supplied at 1200-1600 psi and was also re-circulated through the reactor at a hydrogen to glycerol feed molar ratio of 5:1. In other embodiments, the hydrogen to glycerol feed molar ratio may be between 1:1 to 10:1. Tables 5A and 5B in FIGS. 2A and 2B describe the results with hydrogenolysis of 40% USP grade glycerol feed. Between 47.7-96.4% of the glycerol was converted and between 36.3-55.4% of propylene glycol was produced. In addition to propylene glycol, the hydrogenolysis reaction produced 0.04-2.31% unwanted BDOs, which may present a problem for recovery of pure propylene glycol (Table 6). The BDOs were measured using a known gas chromatography analysis method.

Example 2

Example 2 describes a method to reduce the formation of BDOs and maximize the conversion of glycerol to propylene glycol with a solid phase catalyst such as the "G" catalyst as disclosed in U.S. Pat. No. 6,479,713 or the "HC-1" catalyst available from Süd Chemie (Louisville, Ky.). Hydrogenolysis of a 40% solution of glycerol was carried out substantially as described in Example 1. Table 7 in FIG. 4 describes the conditions used in this Example, and discloses the products produced in this Example.

Example 3

Hydrogenolysis of a 40% solution of glycerol was carried out substantially as described in Example 1. The effect of the reaction temperature at constant concentrations of alkali (sodium hydroxide) and constant LHSV on the amount of BDO formed was investigated. Table 8 in FIG. 5 describes the conditions used in this Example, and discloses the products produced in this Example.

Example 4

Hydrogenolysis of a 40% solution of glycerol was carried out substantially as described in Example 1. The effect of LHSV of the feed at constant concentration of alkali (sodium hydroxide) and constant on amount of BDO formed was investigated. Table 9 in FIG. 6 describes the conditions used in this Example, and discloses the products produced in this Example.

Example 5

Hydrogenolysis of a 40% solution of glycerol was carried out substantially as described in Example 1 except that 180 mL of Süd Chemie HC-1 catalyst was used. The effect of increasing temperature on BDO formation was investigated. Table 10 in FIG. 7 describes the conditions used in this Example, and discloses the products produced in this Example.

Example 6

Hydrogenolysis of a 40% solution of glycerol was carried out substantially as described in Example 1 except that 180 mL of Süd Chemie HC-1 catalyst was used. Table 11 in FIG. 8 describes the conditions used in this Example, and discloses the products produced in this Example.

Example 7

Hydrogenolysis of a 40% solution of glycerol was carried out substantially as described in Example 1, except that 180 mL of Süd Chemie HC-1 catalyst was used. Table 12 in FIG. 9 describes the conditions used in this Example, and discloses the products produced in this Example.

Consequently, as is evident to those skilled in the art suitable conditions exist for hydrogenolysis of glycerol to propylene glycol wherein the yield of propylene glycol is maximized and the formation of BDOs is minimized. Using the embodiments of this invention, one skilled in the art may practice this invention to operate a reactor system and obtain high yields of propylene glycol with low concentrations of BDOs.

The present invention has been described with reference to certain exemplary embodiments, biobased propylene glycol and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

What is claimed is:

1. A composition, comprising:
    a biobased 1,2-propanediol; and
    a weight/weight ratio of polyhydric alcohols other than 1,2-propanediol to the biobased 1,2-propanediol of 0.5% or less, and wherein the polyhydric alcohols present in the composition other than 1,2-propanediol include one or more of 1,2-butanediol, 1,3-butanediol, 1,4-butanediol, 2,3-butanediol and 2,4-pentanediol.

2. The composition of claim 1, further comprising ethylene glycol at a concentration of less than 0.25%.

3. The composition of claim 1, wherein the composition is produced by a process including the hydrogenolysis of glycerol.

4. The composition of claim 1, wherein the weight/weight ratio of the polyhydric alcohols to the biobased 1,2-propanediol is 0.25% or less.

5. A composition, comprising:
a biobased 1,2-propanediol; and
polyhydric alcohols other than 1,2-propanediol, including one or more of 1,2-butanediol, 1,3-butanediol, 1,4-butanediol, 2,3-butanediol and 2,4-pentanediol;
wherein a ratio of the biobased 1,2-propanediol to the other polyhydric alcohols is between 100:1 and 1000:1.

6. The composition of claim 5, further comprising ethylene glycol at a concentration of less than 0.3%.

7. The composition of claim 5, wherein the composition is produced by a process including the hydrogenolysis of glycerol.

8. A composition, comprising:
polyhydric alcohols obtained from a biobased feed stock;
wherein the polyhydric alcohols comprise:
   1,2-propanediol in an amount of at least 997 g/kg on a dry weight basis; and
   one or more of 1,2-butanediol, 1,3-butanediol, 1,4-butanediol, 2,3-butanediol and 2,4-pentanediol, the 1,2-butanediol, the 1,3-butanediol, the 1,4-butanediol, the 2,3-butanediol and the 2,4-pentanediol collectively being present at a concentration of less than 0.5% of the 1,2-propanediol concentration on a dry weight basis.

9. The composition of claim 1, wherein the biobased 1,2-propanediol is present at a concentration of between 0.1% and 99.9% by weight.

10. The composition of claim 5, wherein the biobased 1,2-propanediol is present at a concentration of between 0.1% and 99.9% by weight.

11. The composition of claim 8, wherein the 1,2-propanediol is present at a concentration of between 0.1% and 99.9% by weight.

* * * * *